United States Patent [19]

Howard

[11] 4,335,116

[45] Jun. 15, 1982

[54] MINERAL-CONTAINING THERAPEUTIC COMPOSITIONS

[75] Inventor: James R. Howard, Brawley, Calif.

[73] Assignee: University Patents, Inc., Norwalk, Conn.

[21] Appl. No.: 194,808

[22] Filed: Oct. 7, 1980

[51] Int. Cl.³ .................... A61K 31/68; A61K 31/315
[52] U.S. Cl. .................................... 424/201; 424/131; 424/289; 424/287; 424/295; 424/319
[58] Field of Search ............... 424/319, 289, 201, 287

[56] References Cited

U.S. PATENT DOCUMENTS

| | | | |
|---|---|---|---|
| 2,960,406 | 11/1960 | Cardon | 426/71 |
| 4,020,158 | 4/1977 | Ashmead et al. | 424/319 |
| 4,167,564 | 9/1979 | Jensen | 424/289 |

*Primary Examiner*—Sam Rosen
*Attorney, Agent, or Firm*—Merriam, Marshall & Bicknell

[57] ABSTRACT

Stable aqueous solutions for substantially non-inflammatory, non-immunogenic parenteral administration to domesticated animals, especially livestock animals, comprising water-soluble organometallic complexes of ions of zinc, copper, manganese, chromium and selenium and including at least two organic, metal-ion-complexing agents. Stable solutions further including soluble organometallic complexes of iron and cobalt. Methods for restoring and/or maintaining normal micromineral-dependent metabolic function, increasing feed intake, increasing vigor, and facilitating resistance to infectious disease comprising administering such solutions to domesticated animals.

19 Claims, No Drawings

MINERAL-CONTAINING THERAPEUTIC COMPOSITIONS

BACKGROUND

The present invention relates generally to mineral-dependent metabolic function in domesticated animals and more particularly to novel methods and materials for restoring and maintaining normal growth and development in livestock animals exposed to disruptive environmental conditions such as physical stress, micromineral dietary insufficiency and infectious disease.

While in continuous contact and exchange with the external environment, a living organism engages in continuing chemical change that comprises the organism's metabolism. The control of an organism's multitudinous metabolic processes (and the energy-yielding chemical reactions which make the processes possible) involves highly specific regulatory mechanisms, many of which are sensitive to the presence or absence of certain metallic elements in ionic or specifically chemically complexed forms.

In the higher orders of animals, and especially with respect to humans, the requirements, function and manifestation of deficiency of metallic elements such as sodium, iron, potassium, calcium, magnesium and non-metals such as chlorine and phosphorous are known with relative precision. Despite extensive research efforts, however, such nutritional characteristics for certain of the so-called "microminerals" (including manganese, copper, cobalt, zinc, chromium, selenium and molybdenum) are quite imprecisely know. Indeed, the available research data concerning micromineral nutritive function are often contradictory and/or inconclusive owing to the inordinate difficulty in establishing truly controlled experimental formats. What is known with any degree of certainty of the independent and associative functions of microminerals in the higher animals is frequently derived from in vitro experimentation on specific, isolated metabolic systems. Such information provides little or no guidance to those concerned with the problems of the long range maintenance of growth and development of large numbers of animals such as are encountered in livestock enterprises. The following brief notations of specific micromineral function and interrelations are believed to suitably illustrate the complexity of the state of the art knowledge with respect to micromineral nutrition.

Manganese is believed to have an activating function for many enzymes such as phosphoglucomutase, choline esterase, the oxidative $\beta$-keto-decarboxylases, certain peptidases and muscle ATPase. In man, manganese salts are known to be poorly absorbed through the intestine and the ingestion of large quantities of manganese appears to interfere with the absorption of iron.

Copper's metabolic functions relate to its presence in tyrosinase, urate oxidase, dopamine-$\beta$-hydroxylase, amine oxidases, cytochrome oxidase and cytoplasmic superoxide dismutase (in the latter, in combination with zinc). Copper deficiency in a manner of animals has been consistently correlated with malabsorption of dietary iron. Species-specific symptoms of copper deficiencies include anestrus and abortion in rats, spinal cord demyelinating disorders in sheep and arterial inelasticity in pigs. In the absence of sufficient dietary copper, many herbivores develop anemia and lesions of the skin and bones.

Cobalt is believed to be functional only as a component of vitamin $B_{12}$ and the structurally related cobamide coenzymes which participate in a variety of metabolic functions. Nutritional requirements of these chemically complexed forms of cobalt are ordinarily satisfied by way of absorption of vitamin $B_{12}$ produced by microorganisms comprising the intestinal flora of most higher animals. Omnivorous and carnivorous animals appear not to harbor microorganisms capable of $B_{12}$ production and therefore metabolic requirements must ordinarily be met dietarily. Omnivores and carnivores are thus more readily subject to deficiency diseases.

Zinc is a constituent of numerous enzymes including carbonic anhydrase, the alcohol and lactate dehydrogenases and various peptidases. Zinc deficiencies are subject to widely varying manifestation depending on the species involved: retarded growth, alopecia, and topical lesions in rodents; parakeratosis in pigs; and poor growth and adolescent hypogonadism among humans. In humans, deficiencies are thought to arise most frequently in instances of ingestion of large quantities of a specific hexose phosphate, phytic acid, common in certain cereal grains and suspected of preventing absorption of zinc from the intestine. The same mechanism of deficiency may be involved with domesticated animals.

The status of molybdenum in animal nutrition is quite unclear. It is known to be a constituent of xanthine oxidase and several other enzymes. In herbivora, ingestion of even small amounts of molybdenum inexplicably results in increased copper requirements which, if not met, evoke copper deficiency symptoms.

Selenium function in higher animals is poorly understood. It is believed to combine with enzymes (i.e., glutathione peroxidases) necessary for reinstating cell membrane integrity disrupted by free radicals forming during electron transport in ATP formation. So-called "white muscle disease" in many species of animals as well as liver degeneration and pulmonary edema are frequently associated with selenium-deficient diets but large doses of selenium are known to be extremely toxic.

Chromium has been reported to be significant to proper carbohydrate metabolism in rodents but its specific function in this respect is not clear. It is commonly believed that chromium ions are required for insulin to associate with cell membrane receptor sites and that, in the absence of chromium, insulin-dependent entrance of glucose and acetate ions into cells is diminished.

As might be expected, oral administration of mineral supplements in frequently ineffective in treating deficiency symptoms because the nutritional "problem" often has its origins in malabsorption of particular minerals rather than dietary insufficiency. Parenteral administration of mineral supplements, on the other hand, is almost equally problematic. First, severe difficulties exist in co-solubilizing a plurality of mineral salts, making multiple injections necessary if more than one micromineral is to be administered. Second, many mineral sources are highly inflammatory and destructive of animal tissue when administered intramuscularly or even subcutaneously. Tissue damage is frequently the result of immunological response to the presence of metal ions which appear to operate as haptens. In livestock animals such inflammation and tissue destruction can substantially impair the value of the slaughtered animal.

Adding to the complexity of micromineral nutrition in livestock animals is the fact that maturative processes and environmental variations can precipitously vary the metabolic requirements of animals and hence their need for certain microminerals, frequently elevating the need for those substances which are not stored in any substantial quantity by the animals. Livestock animals express a wide variety of diseases which are known to be environmental stress-related but for which no prophylactic or curative methods and materials are readily available. As one example, sickness is an almost universal consequence of shipment and the transition from range environments and pasture feeding to confinement and so-called high energy concentrate feeding. Many of these disease conditions are felt to be micromineral balance-related. As further examples, animals which have been on micromineral deficient diets for prolonged periods, have endured prolonged systemic infections and/or have had severe diarrhea frequently develop hypogeusia, an apparent alteration in the sense of taste, resulting in progressive diminution of food intake leading to marasmus and death. Such conditions are not known to be treatable by oral administration of microminerals.

Finally, infectious diseases in livestock are also believed to bring about substantial variations in micromineral requirements owing to the involvement of immune system responses which have distinctly different micromineral requirements from those of normal metabolic systems. Correlatively, micromineral insufficiencies or imbalances are believed to impair normal immune function and therefore to contribute to susceptibility to viral and bacterial infection.

As a result of the above-noted complexities, advances in the science of micromineral nutrition have been marginal at best. For the most part, proposals of new methods and materials for restoring and maintaining suitable mineral balances in animals, including livestock animals, have either been overly broad and simplistic or overly narrow and directed to alleviation of symptoms of a specific, manifest micromineral deficiency disease state. The following examples of U.S. Patents relating to mineral nutrition are illustrative of the existing state of the art.

U.S. Pat. No. 2,798,023 relates broadly to oral preparations of "essential vitamins and minerals" especially suitable for ingestion by children and incorporating one or more salts of iodine, manganese, cobalt, potassium, molybdenum, iron, copper, zinc and magnesium. Typifying numerous generalized teachings of the art with respect to human nutrition, this reference ignores many significant aspects of mineral nutrition such as effectiveness of absorption of oral preparations through the intestine and variations in the need for minerals resulting from variations in environmental conditions.

U.S. Pat. No. 3,275,514 to Saltman et al. broadly comprehends the formation of chelates of calcium, magnesium, strontium, barium, titanium, vanadium, chromium, manganese, cobalt, nickel, copper and zinc with so-called "reducing sugars" and advocates, without reservation, the oral, intravenous and/or intramuscular administration of unspecified amounts of any one of all of these chelates.

U.S. Pat. No. 3,975,513 to Hecht et al. relates broadly to treatment of mineral deficiency diseases in young animals. The principal teaching of the patent is the construction and sizing of an iron compound-containing, orally administered bolus so that it will lodge in the stomach and be effective in piglets during the entire period prior to weaning. A collateral teaching of the reference is that unspecified quantities of "trace elements" and fluorine may suitably be administered in a similar manner by imbedding small particles of the elements or their compounds in the thermoplastic polymers from which the boluses are made.

U.S. Pat. No. 4,029,770 to Willard broadly asserts utility for oral and topical application of "catalyst or synergists" to animals with damaged or infected tissue as well as those encountering stress and/or shock. The catalysts consist of alkali metal silicates mixed with magnesium and calcium ion sources and a micelle-forming surfactant.

U.S. Pat. No. 3,829,566 to Burns et al. is specificaly directed to the control of degenerative muscle disease in mammals through administration of an assertedly synergistic combination of vitamin E ($\alpha$-tocopherol) and selenium. The combination is said to be effective when administered parenterally, but orally effective only with non-herbivorous mammals owing to the interfering presence of sulfur, phosphorous and nitrates in customary diets of herbivores.

U.S. Pat. No. 3,923,982 to Lammand provides specific instructions assertedly useful in preventing "trace element deficiency" in animals through parenteral administration of oil suspensions of insoluble, non-ionizable copper, zinc or manganese metals or their oxides. The suspensions are assertedly only "moderately" inflammatory and less seriously tissue-damaging than other metal complexes involving admittedly more readily useful ions of the metals.

The above-noted representative U.S. Patents establish the existance of a long-standing need for nutritive materials and methods for restoring and maintaining normal micromineral dependent growth and development in animals, especially livestock animals, and most especially those exposed to physical stress, debilitating infectious diseases and dietary insufficiency. In their most desirable form, materials responsive to such needs would be characterized by comprehensiveness of micromineral nutrient content, simplicity of formulation, ease of administration, and the relative absence of inflammatory and/or immunogenic effects attending administration. The most desirable nutritive procedures would be characterized by simplicity and long-term efficacy of action in large scale practice involving groups of animals displaying wide variations in maturative state, nutritional history and degree of past or present exposure to infectious disease.

BRIEF SUMMARY

The present invention provides novel micromineral nutritive supplements in the form of stable, homogeneous aqueous solutions adapted for substantially non-inflammatory, non-immunogenic administration to domesticated animals, especially livestock animals. Supplements of the invention are easily formulated and administered and they uniformly operate to enhance and balance micromineral-dependent metabolic function in livestock animals as evidenced by the restoration and/or maintenance of normal growth and developmental patterns (e.g., improvement and continuity in desired weight gain characteristics) as well as by facilitation of resistance to infectious disease (e.g., diminished incidence and/or severity of infection).

According to one aspect of the invention, stable aqueous nutritive supplement solutions are provided which include water soluble organometallic sources of ions of zinc (as $Zn++$), copper (as $Cu++$), manganese (as Mn++), chromium (as Cr+++), and selenium (as Se++). Such solutions may further include a soluble organometallic source of ions of iron (as Fe+++) as well as cobalt (as Co+$^6$) in the form of the organometallic complex, vitamin B$_{12}$.

The remarkably stable and uniform mixtures of metal ion sources are provided by practice of formulation techniques involving use of at least two non-toxic, organic water soluble metal-ion-complexing agents. In one embodiment of the invention, salts of zinc, copper, manganese, and chromium are individually dissolved in water and complexed with a first organic, metal-ion-complexing agent such as the ethylenedinitrilotetraacetic acid ("EDTA") provided to the solution in the form of its tetrasodium salt. The four resulting complexed metal ion solutions are then suitably admixed and, to the combined mixture thus formed, is added an aqueous solution comprising selenium ions complexed with a second organic, metal-ion-complexing agent such as glycine. Iron may then be included in the solution by addition of suitable quantities of ferric ion hydroxide complexed with dextrans or dextrins. Finally, cobalt may be included by addition of an aqueous solution of vitamin B$_{12}$ wherein the cobalt comprises a part of the cyanocobalamin complex.

Specific quantities of individual microminerals provided in the aqueous solutions of the invention may be varied depending on the projected use. As one example, it is within the comprehension of the invention that solutions may be prepared to allow each milliliter thereof to contain: from about 0.1 to about 25 mg of zinc; from about 0.1 to about 10 mg of copper; from about 0.1 to about 20 mg of manganese; from about 0.01 to about 5.0 mg of chromium; and, from about 0.1 to about 12.0 mg of selenium. Iron-containing formulations may include from about 5 to about 300 mg per milliliter of iron and cobalt-containing solutions may include from about 0.001 to 0.5 mg per milliliter of cobalt.

Among the preferred solutions made available according to the invention is one formulated to contain, per milliliter, the following ions: 0.83 mg zinc; 0.17 mg copper; 0.67 mg manganese; 0.03 mg chromium; 0.67 mg selenium; 33 mg iron and 0.005 mg cobalt. Such a preferred solution is particularly useful when parenterally administered, at a dosage level of from about 1 to about 6 milliliters per 100 pounds of body weight, to neonatal animals whose mothers have been on marginally micromineral deficient diets. It is also useful when administered at the same dosage levels to animals which have undergone or will soon undergo stressful environmental changes such as shipping, branding, castration and de-horning, or changes in dietary form such as encountered in transfer from the range to a feedlot.

Another preferred solution made available according to the invention is formulated to contain, per milliliter, the following ions: 4.0 mg zinc; 1.0 mg copper; 3.0 mg manganese; 0.50 mg chromium; and 5.0 mg selenium. This solution, when parenterally administered at a dosage level of from about 1 to 2 milliliters per 100 pounds of body weight, is highly effective in animals maintained over long periods of time on micromineral deficient diets such as frequently provided to fattening cattle in feedlots.

While both of the above-noted preferred solutions are useful in facilitating resistance to infection by viral and bacterial agents, neither is recommended for adminstration during the clinical course of infectious disease owing to potentially adverse immune response stimulation. Expectedly, livestock animals receiving nutritive supplements according to the invention should be maintained on an energy adequate diet, with moldy or otherwise non-nutritive feeds being avoided.

Other aspects and advantages of the present invention will be apparent upon consideration of the following detailed description thereof.

DETAILED DESCRIPTION

The term "ions" when herein employed with respect to zinc, copper, manganese and selenium shall designate divalent forms; when employed with respect to chromium and iron shall designate trivalent forms; and when employed with respect to cobalt shall designate the hexavalent form. "Parenteral" shall mean any administrative mode other than oral and includes subcutaneous, intravenous and intramuscular. "Inflammatory" shall mean giving rise to those localized cytologic and histologic reactions ordinarily designated as inflammation and characterized by the presence of a readily ascertainable degree of one or more of the following: redness, heat, swelling and pain. "Immunogenic" shall mean giving rise to stimulation of the formation of noninfectious swelling characterized by localized, edematous, inflammatory reaction, usually of a delayed type. "Micromineral-dependent metabolic function" designates biochemical reactions, including energy transfers and molecular transport of substances across cell membranes, which require the presence of metals. The term specifically includes biochemical reactions requiring enzymes functionally dependent upon the presence of metal ions in free or complexed forms. "Resistance to infectious disease" shall herein designate the capacity to withstand exposure to a bacterial or viral disease vectors without invasion and/or proliferation of the bacterial or viral agent, as well as to the capacity to minimize the ordinary course of infection. Within a given group of livestock animals, the former type of resistance would be characterized by, e.g., the absence of febrile response or other disease symptoms despite exposure to disease vectors. The latter type of resistance would be characterized by, e.g., a substandard febrile response in terms of severity or duration and/or enhanced effectiveness of standard doses of antibiotic pharmaceuticals (i.e., fewer doses needed to promote recovery). As used herein, "livestock" refers to cattle, sheep and swine. "Increased food consumption" refers to improved assimilation of food by animals with hypoguisea. "Improved vigor" refers to generalized enhancement of the ability of an animal to survive the ravages of severe systemic infection and both physical and emotional stress.

One aspect of the present invention relates to novel methods for preparing stable aqueous solutions suitable for easy parenteral administration to livestock animals, which solutions contain sources of a plurality of metal ions. As previously noted, there exists a problem of long standing in the art attending the preparation of aqueous solutions including a number of metals because the anion of the soluble salt of one metal will frequently associate with metal cations provided to a mixture of solutions of metals salts and precipitate the other metal cations as insoluble salts. By way of illustrative example, the admixture of solutions of silver nitrate and sodium chloride will result in the formation of an insoluble silver chloride precipitate.

The formulative techniques of the present invention provide for the preparation of homogenous solutions providing sources of zinc, copper, manganese, chromium and selenium through use of at least two metal-ion-complexing agents. The preferred techniques involve the formation of separate solutions of complexes of zinc, copper, manganese and chromium with a single organic complexing agent such as ethylenedinitrilotetraacetic acid. The separate solutions of organometallic complexes so formed are admixed to develop a first solution component. A second solution component is prepared by forming an organometallic complex including selenium. Preferred complexing agents for selenium are organic substances forming zwitterions in aqueous solution such as the amino acids. The most preferred selenium complexing agent is glycine. First and second solution components are then mixed to form the final stable aqueous solution. Iron can be incorporated into such solutions by the simple step of adding a solution of iron in readily available dextran- or dextrin-complexed form. Cobalt can also be incorporated by additions of a soluble vitamin $B_{12}$ complex.

Practice of the formulative techniques of the invention is illustrated by the following examples.

EXAMPLE 1

This example relates to the preparation of a stable aqueous solution containing, per milliliter, about 4.0 mg zinc ion, 1.0 mg copper ion, 3.0 mg manganese ion, 0.50 mg chromium ion and 5.0 mg selenium ion. All procedures are carried out at room temperature unless otherwise indicated.

A solution is prepared by dissolving 53.8 grams of the tetrasodium salt of ethylenedinitrilotetraacetic acid ("EDTA") in 250 ml water.

A zinc/EDTA complex is formed by first dissolving 8.36 grams of zinc chloride in 200 ml water and adding 108.75 ml of the above EDTA solution. Precipitating material is redissolved by pH adjustment using hydrochloric acid. The solution is set aside overnight or heated for a few hours at about 50° C. to accelerate zinc/EDTA complex formation. Any precipitate formed is redissolved with HCl.

A copper/EDTA complex is formed by first dissolving 2.68 grams of copper chloride (dihydrate) in 40 ml water and adding 27.75 ml of the above EDTA solution. The solution is set aside for several hours to allow for stabilization of the copper/EDTA complex. No pH adjustment is ordinarily required to avoid precipitate formation with these quantities of materials.

A manganese/EDTA complex is formed by dissolving 10.8 grams manganese chlordie (tetrahydrate) in 150 ml water and adding 96.5 ml of the above EDTA solution. After pH adjustment with HCl to dissolve any precipitate formed, the solution is allowed to stand overnight or heated a few hours at 50° C. to accelerate manganese/EDTA complex formation. Further pH adjustment may be required to develop a stable, precipitate-free solution of the complex.

A chromium/EDTA solution is formed by first dissolving 2.56 grams of chromium chloride (hexahydrate) in 50 ml water. Five ml of this solution is added to a mixture of 50 ml water and the remaining 17.0 ml of EDTA solution. Any precipitate formed is redissolved by pH adjustment with HCl. Thereafter, the remaining 45 ml of chromium chloride solution is added gradually, with pH adjustments as needed to develop a clear purple solution of chromium/EDTA complex.

The above-formed solutions of EDTA complexes of zinc, copper and manganese are admixed and allowed to stand overnight or gently heated for a few hours. To this mixture is added the chromium/EDTA solution and the entire mixture, comprising the first solution component, is allowed to stand for about one hour.

A selenium/glycine complex solution providing the second solution component is formed by first dissolving 13.14 grams of sodium selenite in 75 ml water. To this is gradually added, with mixing, a solution of 11.4 ml glycine and 75 ml water. The mixture is allowed to stand for about one hour.

The first and second solution components are then mixed together and the total volume is adjusted to 1 liter with water and a bactericidal agent such as benzyl alcohol.

EXAMPLE 2

This example relates to preparation of one liter of a stable aqueous solution containing, per milliliter, about 0.83 mg zinc ion, 0.17 mg copper ion, 0.67 mg manganese ion, 0.03 mg chromium ion, 0.67 mg selenium ion, 33 mg iron ion and 0.005 mg cobalt ion.

The procedure of Example 1 is followed to prepare a mixture of the EDTA complexes of zinc, copper, manganese and chromium with a glycine/selenium complex. The specific quantities of materials involved are as follows: 10.793 grams EDTA (sodium salt); 1.733 grams zinc chloride; 0.447 grams copper chloride; 2.4 grams manganese chloride; 0.17 grams chromium chloride; 1.46 grams sodium selenite; and 1.283 gm glycine. To this mixture is added 11 ml of a one percent solution of vitamin $B_{12}$, 5 ml benzyl alcohol and 330 ml of 10 percent (by weight, iron) solution of iron dextran. Water is employed throughout in quantities bringing the final volume to one liter.

While the above Examples 1 and 2 each employ chloride salts of zinc, copper, manganese and chromium, it will be understood that the soluble metal salts of other anions may be employed. Likewise, selenium ion sources other than sodium selenite may be employed. While the examples refer to the sodium salt of ethylenedinitrilotetraacetic acid as the preferred complexing agent for zinc, copper, manganese and chromium, such organic agents as sodium citrate are expected to be equally suitable. While glycine is the preferred complexing agent for selenium, other amino acids or similar compounds forming zwitterions in aqueous solution are expected to be equally useful.

Stable aqueous solutions prepared in the manner of Examples 1 and 2 are, according to another aspect of the invention, useful as substantially non-inflammatory, non-immunogenic materials for parenteral administration to livestock animals to enhance micromineral-dependent metabolic function and resistance to infectious disease.

As previously noted, parenteral administration of microminerals in aqueous ionic forms is generally problematic owing to the marked inflammation and immunogenic response developed at sites of injection. These deleterious responses are so severe in some cases (ranging in size up to 20 cm in diameter and 5 cm thick) that they can be avoided only by intravenous administration of the highly irritating materials. Evidence of immunogenic response to intramuscular administration of bi- and tri-valent cations in aqueous solutions is usually provided by the presence, from ten to twenty days after injection, of marked edematous and inflammatory reactions. The ions appear to react with body tissue and act as haptens which stimulate an immune response. Subsequent injections of ion solutions result in the same reaction in from three to five days. Commerically available copper glycinate requires administration in the dewlap in cattle to minimize damage from necrosis and abcesses. Commercially available sodium selenite solutions are known to cause swelling and irritation at the injection site within hours and from ten to twenty-five percent of the recipients have immunogenic reactions. None of these pronounced reactions is observed upon administration of solutions of Example 2 and the solutions of Example 1 are minimally irritating—causing small (5 cm by 1 cm) transitory edematous reactions within three to four days after administration.

Solutions of the invention are easily and uniformly administered due to their stable, homogeneous nature. In this regard, they are quite unlike, e.g., copper glycinate suspensions which are difficult to mix uniformly and which tend to settle out during use. The solutions of Examples 1 and 2 are promptly effective even when administered subcutaneously.

While solutions of the invention as prepared according to Examples 1 and 2 may be formulated to incorporate up to 25 mg zinc ions, 10 mg copper ions, 20 mg manganese ions, 5 mg chromium ions, and 12 mg selenium ions per milliliter, care should be taken to avoid giving excessive amounts of such high concentration solutions. It has been noted, for example, that injection of solution volumes providing more than about 5 mg of zinc or manganese or selenium ions per 100 pounds of animal body weight, though not toxic, will not likely result in desired improvements in weight gain characteristics and may in fact suppress weight gain.

Consistent with the above, administration of from about 1 to about 6 ml of the Example 2 solution per 100 pounds body weight has been found to be useful when provided to neonatal calves, to animals just before or after shipping stresses and/or introduction to a feed lot environment, and even when given to adult animals during "accelerated" growth and fattening in feed lots. For the last-mentioned animals, it is preferred to administer 1 or perhaps 2 ml of the Example 1 solution per hundred pounds of body weight, with the initial dosage given about 60 days after arrival at the feedlot and repeated every 60 to 100 days thereafter. Administration of either type of solution should be avoided during the clinical course of infection. The following examples relate to the effectiveness of administration of solutions of the invention.

EXAMPLE 3

Tests were conducted on three loads of 300 pound mixed-bred beef calves provided by order buyers in three different locations in Texas. The exact geographical origins of the calves was unknown, but most were likely to have been from Texas with a few from south central and southeastern states. All calves had gone through at least one auction sale where they were exposed to systemic virus infection. They arrived in the Imperial Valley in May and during the ensuing three weeks experienced about ten days of stressful hot weather. These calves had been fed high concentrate starting rations with free choice musty sudan or lush alfalfa (a feeding combination almost certain to increase incidence and severity of shipping fever). The calves were divided between two feedlots, and were processed within 2 days of arrival. Processing consisted of horntipping, branding, castrating, injection with one million units vitamin A, and eartagging with small sequentially numbered tags. At this time test injections of the solution of Example 2 were given, 3 ml per 100 pounds subcutaneously. Test treatements were alternated with controls as calves went through the chute for processing. All calves in each load were penned together and each day sick calves were sorted from the pens and treated with antibiotics. Daily records were kept of work done on any animal.

In the following table the data of these three trials is summarized.

TABLE I

| Shipping Fever Therapy Response | Control Animals | Solution Treated Animals |
| --- | --- | --- |
| Healthy-Not Sick | 43% | 45% |
| Good[1] | 37% | 39% |
| Poor[2] | 9% | 14% |
| Death Loss | 12% | 1% |
| No. in Test | 80 | 77 |

[1]Animals receiving 4 antibiotic treatments or less for shipping fever.
[2]Animals receiving more than 4 antibiotic treatments for shipping fever.

Results of these tests indicate that the solution did not significantly reduce incidence of sickness. About the same number of calves remained healthy in each group, probably owing to the calves being sick with systemic infections at the time of treatment. Nor was there any appreciable change in the percentage of calves having a favorable response to shipping fever therapy (only two percentage points difference in the combined trials). As for poor response to shipping fever therapy, the treated calves had a five percent increase in poor response. This increase may represent an upgrading from death loss to poor responding survivors. Calves that would have died had they not received the solution required more antibiotic treatments but lived because they were given the test material.

There was a sizable decrease in death loss among the treated calves, 11%, indicating enhanced vigor. Many of the control animal deaths were what are referred to as stress related. With little if any evidence of infectious disease, the dead calves had hitologic changes in parenchymatous tissue such as liver and kidneys. The test solution did enhance metabolic function as was evidenced by a 15.9 percent improvement in weight gain as compared to controls. It also aided the ability to withstand the stresses of shipping and adapting to new feeding practices. On this latter point, a 12 percent average death loss of the control calves was high for the industry overall. It is likely that it represents the consequences of feeding high energy starting feed in combination with lush alfalfa or musty sudan. This could have led to mild grain overload or decreased energy consumption, either of which would tend to exaggerate metabolic disturbances.

EXAMPLE 4

This example illustrates the general absence of desired effectiveness of solutions of the invention when administered to animals during the course of infectious disease. A test was conducted with 135 pound Holstein calves that had been weaned at 6 weeks of age and shipped from central California to the Imperial Valley. They arrived in June when it was hot and the feed they were given was unpalatable to them so they ate very little. The protocol for the test, which was set up eleven days after arrival in the yard was similar to that of Example 3. The calves were run through a chute and small sequentially-numbered eartags were applied. Every other calf was given 3 ml of the Example 2 solution per 100 pounds of body weight. All calves were penned together and records were kept of calves treated for shipping fever (ten days) and deaths (21 days). A summary of results is set out in the following table.

TABLE II

| Shipping Fever Therapy Response | Control Animals | Treated Animals |
|---|---|---|
| Healthy at 10 days | 47% | 31% |
| Good at 10 days | 33% | 39% |
| Poor at 10 days | 8% | 16% |
| Death Loss at 21 days | 12% | 14% |
| No. in Test | 49 | 49 |

In this instance there were adverse health effects from the injection of the test solution. At the time the test was started calves were dying and many had been treated for shipping fever.

EXAMPLE 5

This example illustrates general effectiveness of solutions of Example 2 on chronically ill and debilitated cattle. Calves that have sustained a severe systemic infection such as shipping fever may develop hypogeusia and marasmus characterized by loss of appetite, wasting, termination by infectious disease. The Example 2 solution was tested in a group of 150 pound Holstein calves with this condition in an Imperial Valley feedlot. These calves had been in the lot 20 to 40 days and had gone through a shipping fever epizootic. There were about 200 calves in the group. They were dying at a rate of six to ten per day, feed consumption was minimal and all anitbiotic treatments were to no avail. The protocol was similar to the Example 4 test on clinically ill calves with the exception that only death losses were noted. The following table provides a summary of the test results.

TABLE III

|  | Control Animals | Treated Animals |
|---|---|---|
| Death Loss | 40% | 26% |
| No. in Test | 47 | 47 |

Death losses were consistent in the control group, 2 to 3 per day. In the treated calves no deaths occurred until the fourth to sixth days when most of the calves died, then losses remained at a low inconsistant rate for the rest of the study with the overall change in loss rate due to the solution being a 35% relative decrease. The losses of the treated calves are thought to have been due to their being actively infected with IBR virus at the time of infection.

A second test was made in calves debilitated after going through a shipping fever epizootic. Appetites were depressed and the calves were in various stages of marasmus. These were 300 pound crossbred calves originating from Texas that were culled from 700 head shipped into a feedlot in May. They were treated with the Example 2 solution about 30 days after arrival in the feedlot, on a rotational basis as they went through a chute. The following table provides a summary of the test results.

TABLE IV

|  | Control Animals | Treated Animals |
|---|---|---|
| Death Loss | 14% | 3% |
| No. in Test | 37 | 36 |

In this test, treated calves responded to the treatment with improved survival, a 79 percent relative increase overall. Treated calves showed improved appetite and within a week or two show marked improvement in heatlh. It was also observed that if injection of the Example 2 solution is repeated in severely debilitated calves in 14-20 days further improvement is experienced with no relapses occurring. A single injection may be followed by return of debilitation in 15-30% of cases.

EXAMPLE 6

A series of nine studies was conducted to evaluate the effectiveness of solutions of Example 2. In each of the studies, treated calves were injected with 3 ml per 100 pounds weight of the solution at the time of arrival at the feedlot. Treatments were alternated with control animals as the calves went through the chute. Each animal was ear-tagged and weighed. Treated and control animals in each study were kept in a common pen. All aminals had been trucked to the Imperial Valley from order buyers in Texas and has originated from a total of 4 sources ("A" through "D"). Daily records were kept for shipping fever and each calf was reweighed at the end of the 60-day study. Table V below summarizes the data from each of the nine studies.

TABLE V

| Study | Animals in Group | % Remaining Healthy | Sick-Calf Response to Treatment | | % Change ADG | % Death Loss | Source | Treatment |
|---|---|---|---|---|---|---|---|---|
| | | | % Satisfactory | % Unsatisfactory | | | | |
| I | 42 | 48 | 40 | 12 | | 4.8 | A | Control |
| | 42 | 45 | 43 | 12 | 4 ↓ (−) | 2.4 | | Treated |
| II | 17 | 18 | 41 | 41 | | 0 | B | Control |
| | 17 | 24 | 24 | 53 | 2.1 ↑ (+) | 0 | | Treated |
| III | 19 | 11 | 68 | 21 | | 0 | B | Control |
| | 18 | 0 | 56 | 44 | 6 ↑ (+) | 0 | | Treated |
| IV | 39 | 38 | 49 | 13 | | 0 | A | Control |
| | 39 | 56 | 31 | 13 | 4.2 ↑ (+) | 0 | | Treated |
| V | 13 | 62 | 31 | 8 | | 0 | B | Control |
| | 13 | 38 | 38 | 23 | 3.5 ↑ (+) | 0 | | Treated |
| VI | 17 | 6 | 59 | 35 | | 5.9 | B | Control |
| | 17 | 18 | 12 | 71 | 28 ↓ (−) | 0 | | Treated |
| VII | 20 | 30 | 35 | 35 | | 0 | C | Control |
| | 20 | 30 | 50 | 20 | 15 ↑ (+) | 0 | | Treated |
| VIII | 7 | 57 | 29 | 14 | | 0 | A | Control |
| | 7 | 71 | 29 | 0 | 4 ↑ (+) | 0 | | Treated |
| IX | 15 | 40 | 20 | 40 | | 0 | D | Control |

TABLE V-continued

| Study | Animals in Group | % Remaining Healthy | % Satisfactory | % Unsatisfactory | % Change ADG | % Death Loss | Source | Treatment |
|---|---|---|---|---|---|---|---|---|
| | | | Sick-Calf Response to Treatment | | | | | |
| | 15 | 60 | 33 | 7 | 5↑(+) | 0 | | Treated |
| Comparison of Treatments; Number of Studies Showing Superiority | | | | | | | | |
| | 3 | 4 | 4 | 2 | | | | Control |
| | 5 | 4 | 3 | 7 | | 2 | | Treated |
| | 1 | 1 | 2 | 0 | | 7 | | Equal |

The above data demonstrates efectiveness of the treatment in reducing death loss (especially if the single treated animal death in Study I is discounted on grounds of death due to bloat), reducing sickness, and increasing weight gain (ADG values are "average daily gain" throughout the study). It should be noted that in the four studies wherein there was a relatively "unsatisfactory" response for test animals to antibiotic treatment of sick calves (4 or more antibiotic treatments needed), all calves originated from the same source, suggesting that an unknown factor peculiar to the source adversely affected antibiotic treatment response.

While no controlled tests on disease prevention have been made involving solutions of the invention, there have been no virus disease "breaks" during the finishing period in cattle which have been treated at the recommended dose. Treatment virtually eliminated chronic pneumonia, atypical interstitial pneumonia, recrudescence of Infectious Bovine Rhinotracheitis, progressive virus pneumonia and heat related deaths during the growing and finishing of feedlot cattle, as this condition is not seen in feedlots where the solution is routinely used. One slatted floor confinement feedlot was losing about 5% of its heavy cattle due to intractable bacterial infections metastasizing from small skin injuries. Routine use of the solution has eliminated these losses. Also heat related deaths caused by diaphragm muscle degeneration are virtually eliminated.

A few studies on weight gain have been made. Generally, they are positive but occasionally they are null to slightly negative. Results in the latter case appear to be related to soil characteristics at origin and to type of cattle. Large feeders originating from Imperial Valley pasture backgrounds having adequate micromineral soil concentrations were not benefited by treatment. Similar cattle from mountainous terrain or from California, Nevada, Utah or Arizona ranges where trace mineral imbalances are common were benefited by solution injections.

Variability in response to the solutions in the above examples appears to have been due to micronutrient reserves in the tissues of the cattle tested and variations in formulations of feed. The most beneficial response to treatment are seen in cattle that are small when they come into the feedlot, and that are "pushed" to gain maximally during the early and middle parts of the feeding period. Either the ability of these calves to gain exceeds their ability to absorb micronutrients or the micronutrients are not adequate in the ration. Slower growing calves do not respone to the solutions as well as the faster gainers on a general basis.

Numerous modifications on variations in practice of the invention in its several aspects as above-described are expected to occur to those of skill in the art. Consequently, only such limitations as are set out in the appended claims should be placed thereon.

What is claimed is:

1. A stable aqueous solution adpated for substantially non-inflammatory, non-immunogenic parenteral administration to domesticated animals to enhance micromineral-dependent metabolic function and facilitate resistance to infectious disease, said aqueous solution consisting of:
    (a) a water soluble source of selenium ions in the form of an organometallic complex with an amino acid metal-ion-complexing agent; and,
    (b) water soluble sources of zinc, copper, manganese and chromium ions in the form of organometallic complexes with ethylenedinitrilotetraacetic acid,
    said stable aqueous solution containing, per milliliter volume, from about 0.1 to about 25 mg zinc ions, from about 0.1 to about 10.0 mg copper ions, from about 0.1 to about 20.0 mg manganese ions, from about 0.1 to about 5.0 mg chromium ions, and from about 0.1 to about 12.0 mg selenium ions.

2. A solution according to claim 1 wherein said amino acid is glycine.

3. A solution according to claim 1 further including a soluble source of iron ions in the form of a water soluble organometallic complex with dextrans or dextrins.

4. A solution according to claim 3 wherein each milliliter volume contains from about 10 to about 300 mg of iron ions.

5. A solution according to either of claims 1 or 3 further including cobalt ions in the form of a water soluble vitamin $B_{12}$ complex.

6. A solution according to claim 5 wherein each milliliter volume contains from about 0.005 to about 0.5 mg cobalt ions.

7. A method for enhancing micromineral-dependent metabolic function and facilitating resistance to infectious disease in livestock animals, said method comprising parenterally administering a nutritionally effective quantity of a stable aqueous solution according to claim 1.

8. A method according to claim 7 wherein, in said aqueous solution, zinc, copper, manganese and chromium ions are complexed with ethylenedinitrilotetraacetic acid and selenium ions are complexed with glycine.

9. A method according to claim 7 wherein said aqueous solution further contains, per milliliter volume, from about 10 to 300 mg iron ions in the form of a water soluble complex with dextrans or dextrins.

10. A method according to either of claims 7 or 9 wherein said solution further contains, per milliliter volume, from about 0.005 to about 0.5 mg cobalt ions in the form of a soluble vitamin $B_{12}$ complex.

11. A method according to claim 7 wherein the amount of solution administered is from 1 to 6 ml per 100 pounds of body weight.

12. A stable aqueous solution adapted for substantially non-inflammatory, non-immunogenic parenteral administration to domesticated animals, especially livestock animals, to enhance micromineral-dependent metabolic function, improve vigor, increase feed intake and facilitate resistance to infectious disease, each milliliter of said aqueous solution consisting of:
  (a) a water soluble source of about 0.67 mg selenium ion in the form of an organometallic complex with an amino acid metal-ion-complexing agent; and,
  (b) water soluble sources of about 0.83 mg zinc ions, 0.17 mg copper ions, 0.67 mg manganese ions, and 0.50 mg chromium ions in the form of organometallic complexes with ethylenedinitrilotetraacetic acid.

13. A solution according to claim 12 wherein said amino acid is glycine.

14. A solution according to claim 12 further including, per milliliter volume, about 33 mg iron ions in the form of a water soluble organometallic complex with dextrans or dextrins.

15. A solution according to either of claims 12 or 14 further including about 0.005 mg cobalt ions in the form of a water soluble vitamin $B_{12}$ complex.

16. A stable solution adapted for substantially non-inflammatory, non-immunogenic parenteral administration to domesticated animals, especially livestock animals, to enhance micromineral-dependent metabolic function, improve vigor, increase feed intake, and facilitate resistance to infectious disease, each milliliter of said aqueous solution consisting of:
  (a) a water soluble source of about 5.0 mg selenium ion in the form of an organometallic complex with an amino acid metal-ion-complexing agent; and,
  (b) water soluble sources of about 4.0 mg zinc ions, 1.0 mg copper ions, 3.0 mg manganese ions, and 0.50 mg chromium ions in the form of organometallic complexes with ethylenedinitrilotetraacetic acid.

17. A solution according to claim 16 wherein said amino acid is glycine.

18. A method for preparing a stable aqueous solution of metal ions, said method comprising:
  (a) forming a first solution component by forming a solution of an organometallic complex of ions of selenium with an amino acid metal-ion-complexing agent;
  (b) forming a second solution component by separately forming solutions of organo-metallic complexes of ions of zinc, copper, manganese and chromium with ethylenedinitrilotetraacetic acid and admixing said separately-formed solutions of complexes; and
  (c) admixing said first and second solution components.

19. A method according to claim 18 wherein, in forming said first solution component, glycine is the amino acid employed as the complexing agent.

* * * * *

UNITED STATES PATENT AND TRADEMARK OFFICE
CERTIFICATE OF CORRECTION

PATENT NO. : 4,335,116
DATED : June 15, 1982
INVENTOR(S) : JAMES R. HOWARD

It is certified that error appears in the above-identified patent and that said Letters Patent are hereby corrected as shown below:

Col. 1, line 32, "know" should be --known--.

Col. 5, line 19, after "organic," insert --amino acid--.

Col. 7, line 52, "chlordie" should be --chloride--.

Col. 12, line 44, "has" should be --had--.

Col. 13, line 61, "respone" should be --respond--.

Col. 13, line 63, "on" should be --and--.

Signed and Sealed this

Twenty-third Day of November 1982

[SEAL]

Attest:

GERALD J. MOSSINGHOFF

Attesting Officer    Commissioner of Patents and Trademarks